(12) United States Patent
Oliver et al.

(10) Patent No.: US 7,927,361 B2
(45) Date of Patent: Apr. 19, 2011

(54) METHOD AND APPARATUS FOR REMOVING MATERIAL FROM AN INTERVERTEBRAL DISC SPACE, SUCH AS IN PERFORMING A NUCLEOTOMY

(75) Inventors: Dana A. Oliver, Jacksonville, FL (US); Kenneth M. Adams, Bonita Springs, FL (US); Tom J. Francis, Cordova, TN (US)

(73) Assignee: Medtronic Xomed, Inc., Jacksonville, FL (US)

(*) Notice: Subject to any disclaimer, the term of this patent is extended or adjusted under 35 U.S.C. 154(b) by 1083 days.

(21) Appl. No.: 11/289,266

(22) Filed: Nov. 29, 2005

(65) Prior Publication Data
US 2007/0149975 A1 Jun. 28, 2007

(51) Int. Cl.
*A61B 17/88* (2006.01)
(52) U.S. Cl. .................. 606/279; 606/79; 606/86 R
(58) Field of Classification Search .............. 606/79, 606/80, 279, 86 R, 114, 115, 96, 97, 98, 99
See application file for complete search history.

(56) References Cited

U.S. PATENT DOCUMENTS

| 4,573,448 A * | 3/1986 | Kambin ............. 606/170 |
| 5,286,253 A * | 2/1994 | Fucci ............... 604/22 |
| 5,313,962 A * | 5/1994 | Obenchain ........ 128/898 |
| 5,383,884 A | 1/1995 | Summers |
| 5,540,708 A * | 7/1996 | Lim et al. ......... 606/170 |
| 5,911,701 A * | 6/1999 | Miller et al. ......... 604/22 |
| 5,925,056 A | 7/1999 | Thomas et al. |
| 5,980,504 A * | 11/1999 | Sharkey et al. ....... 604/510 |
| 6,312,438 B1 * | 11/2001 | Adams ............. 606/159 |
| 6,440,138 B1 * | 8/2002 | Reiley et al. ........ 606/79 |
| RE38,018 E * | 3/2003 | Anctil et al. ........ 606/170 |
| 7,276,074 B2 * | 10/2007 | Adams et al. ....... 606/170 |
| 2002/0038130 A1 * | 3/2002 | Adams ............. 606/170 |
| 2002/0138091 A1 | 9/2002 | Pflueger |
| 2003/0191474 A1 * | 10/2003 | Cragg et al. ........ 606/79 |
| 2004/0127927 A1 | 7/2004 | Adams |
| 2005/0065538 A1 | 3/2005 | Van Wyk |
| 2005/0159767 A1 | 7/2005 | Adams et al. |
| 2005/0209610 A1 * | 9/2005 | Carrison ........... 606/114 |
| 2006/0149268 A1 * | 7/2006 | Truckai et al. ....... 606/79 |

FOREIGN PATENT DOCUMENTS
WO  WO2005046492  5/2005

OTHER PUBLICATIONS
The PCT International Search Report mailed Mar. 15, 2007 (7 pgs.).
* cited by examiner

*Primary Examiner* — Eduardo C Robert
*Assistant Examiner* — Jan Christopher Merene
(74) *Attorney, Agent, or Firm* — Dicke, Billig & Czaja, PLLC (57) ABSTRACT

Instrument and method for removing material from an intervertebral disc. The instrument includes outer and inner tubular members. The outer tubular member defines a passage and a cutting window. The inner tubular member is coaxially disposed within the passage, and defines a central lumen and a cutting tip. The cutting tip forms an open mouth having a plurality of teeth. Upon assembly, the cutting tip is exposed within the cutting window combining to define a shaving head. A powered handpiece is coupled to the inner tubular member, and the shaving head is inserted into an intervertebral disc and positioned such that the cutting tip contacts targeted material (e.g., nucleus, annulus and/or end plate). The handpiece is activated to rotate the cutting tip relative to the cutting window. Contacted material is sheared between an edge of the cutting window and the teeth of the cutting tip.

17 Claims, 7 Drawing Sheets

METHOD AND APPARATUS FOR REMOVING MATERIAL FROM AN INTERVERTEBRAL DISC SPACE, SUCH AS IN PERFORMING A NUCLEOTOMY

BACKGROUND OF THE INVENTION

The present invention relates to removal of intervertebral disc material. More particularly, it relates to a method and powered device for removing some or all of the material (tissue, cartilaginous bone, etc.) associated with an intervertebral disc, for example in performing a nucleotomy.

The vertebral spine includes, amongst other structures, a series of bony vertebrae, adjacent ones of which are supported and separated by an intervertebral disc. In a healthy spine, the discs maintain separation between the vertebrae, promoting fluid circulation throughout the spine, and providing a cushioning effect between the vertebral structures. An intervertebral disc generally includes an annulus fibrosis (or "annulus"), a nucleus pulposus (or "nucleus"), and opposing end plates. The end plates are akin to cartilaginous bone and serve to attach adjacent vertebrae to the disc. The nucleus is disposed between the end plates, circumferentially constrained by the annulus.

Intervertebral discs are elastic in nature, and can be damaged or displaced. For example, intervertebral discs can be overtly stressed by excessive movement, excess body weight, injury, disease, and/or gradual deterioration with age. Intervertebral disc injuries or other abnormalities can result in serious back pain and physical disability, and are often chronic and difficult to treat. For example, the annulus may bulge or tear, with the distended nucleus tissue compressing against a spinal nerve (e.g., disc herniation). Similarly, the disc may degenerate over time, leading to a collapse of the disc space.

Surgical procedures have been developed to repair damage or displaced intervertebral discs. These procedures include nucleotomies or discectomies in which a portion (e.g., the nucleus), or an entirety of the intervertebral disc is excised. Fusion is another accepted technique and entails the bony portions of the spine being fused together to limit the relative motion between adjacent vertebrae. Insertion/implantation of the fusion-inducing device(s) again requires removal of certain discal tissue. Similarly, disc decompression/fusion procedures require forming a hole in the annulus possibly followed by removal of nucleus tissue prior to backfilling with fusion material. More recently, nucleus replacement implants have been developed; these products also require removal of discal tissue (i.e., the nucleus and/or portions of, or all of, the annulus) prior to implantation.

Regardless of the exact procedure, various manual instruments for the removal of intervertebral disc material(s) are conventionally employed. These manual instruments include osteotomes, surgical chisels, guillotine cutting devices, etc. The highly confined nature of the surgical site associated with the intervertebral disc, the delicate surrounding structures (e.g., nerves), and the wide-range of material to be cut (i.e., the nucleus tissue is fairly soft, whereas the annulus tissue is quite tough), have likely given rise to the reliance upon simple, manual devices. While viable, use of manual instrumentation can render the procedure overly time consuming. Often times, several different manual instruments must be passed in and out of the surgical site multiple times in order to remove the desired discal material. This increases the chance of damage to sensitive structures adjacent to the spine (vascular and nervous). The manual instruments also require separate irrigation and suction device(s) to clean the surgical site during and after the procedure. Further, for certain procedures such as nucleotomies, manual surgical instruments require a surgeon to rely upon tactile feel to ensure that the annulus is not violated.

Injured and degenerated intervertebral discs pose serious health problems to a large number of patients. Many current and future treatments require the removal of nucleus and/or other discal tissue. Manual intervertebral disc material-removing tools are time-consuming to use, and require multiple other instruments. Available powered instruments for cutting intervertebral disc material do not afford the ability to deftly shave only targeted bodily structures, an attribute essentially required by the anatomy forming and surrounding the intervertebral disc. Further, available powered instruments may not be able to adequately cut the disparate bodily materials (in terms of hardness and toughness) typically presented by an intervertebral disc. Any advancement in the tools and related methods for performing this delicate material removal within or at the disc space will be well-received.

SUMMARY OF THE INVENTION

Some aspects of the present invention relate to a method of removing material from an intervertebral disc otherwise defined by a nucleus surrounded by an annulus and opposing end plates. The method includes providing a surgical shaving instrument including an elongated outer tubular member and an elongated inner tubular member. The outer tubular member defines a central passage and a cutting window at a distal end thereof. The cutting window is defined by a perimeter edge and is fluidly connected to the central passage. The inner tubular member is coaxially disposed within the central passage, and further defines a central lumen and a cutting tip at a distal end thereof. The cutting tip forms a mouth that is open to the lumen and has a plurality of teeth formed along a perimeter. Upon final assembly, the cutting tip is exposed within the cutting window, with the cutting tip and cutting window combining to define a bodily material shaving head. A powered handpiece is coupled to the inner tubular member such that the powered handpiece can cause the inner tubular member to rotate relative to the outer tubular member. The shaving head is inserted into an intervertebral disc and positioned such that the cutting tip contacts targeted material of the disc. The powered handpiece is activated to rotate the cutting tip relative to the cutting window. Contacted bodily material is, as a result, sheared between the edge of the cutting window and the teeth of the cutting tip. Finally, the sheared material is aspirated through the inner tubular member's lumen via the mouth. In one embodiment, the surgical instrument further includes an irrigation mechanism fluidly connected to the bodily material shaving head, with the method further including irrigating the material shaving head while shearing tissue.

Other aspects of the present invention relate to a surgical intervertebral disc material shaving instrument for use with a powered handpiece. The instrument includes outer and inner tubular members. The outer tubular member defines a central passage and a cutting widow. The cutting window is fluidly connected to the central passage and is defined by a perimeter edge having opposing, first and second longitudinal sides. At least four teeth are formed on each of the opposing longitudinal sides. The inner tubular member is coaxially disposed within the central passage, and defines a central lumen and a cutting tip. The cutting tip forms a plurality of circumferentially-extending teeth about a mouth that is otherwise fluidly connected to the lumen. Upon final assembly, the cutting tip is exposed within the cutting window, with the cutting window and the cutting tip combining to define a material shaving head adapted to shear intervertebral disc material, as well as to aspirate sheared material through the mouth and lumen.

DETAILED DESCRIPTION OF THE INVENTION

Figure 1:
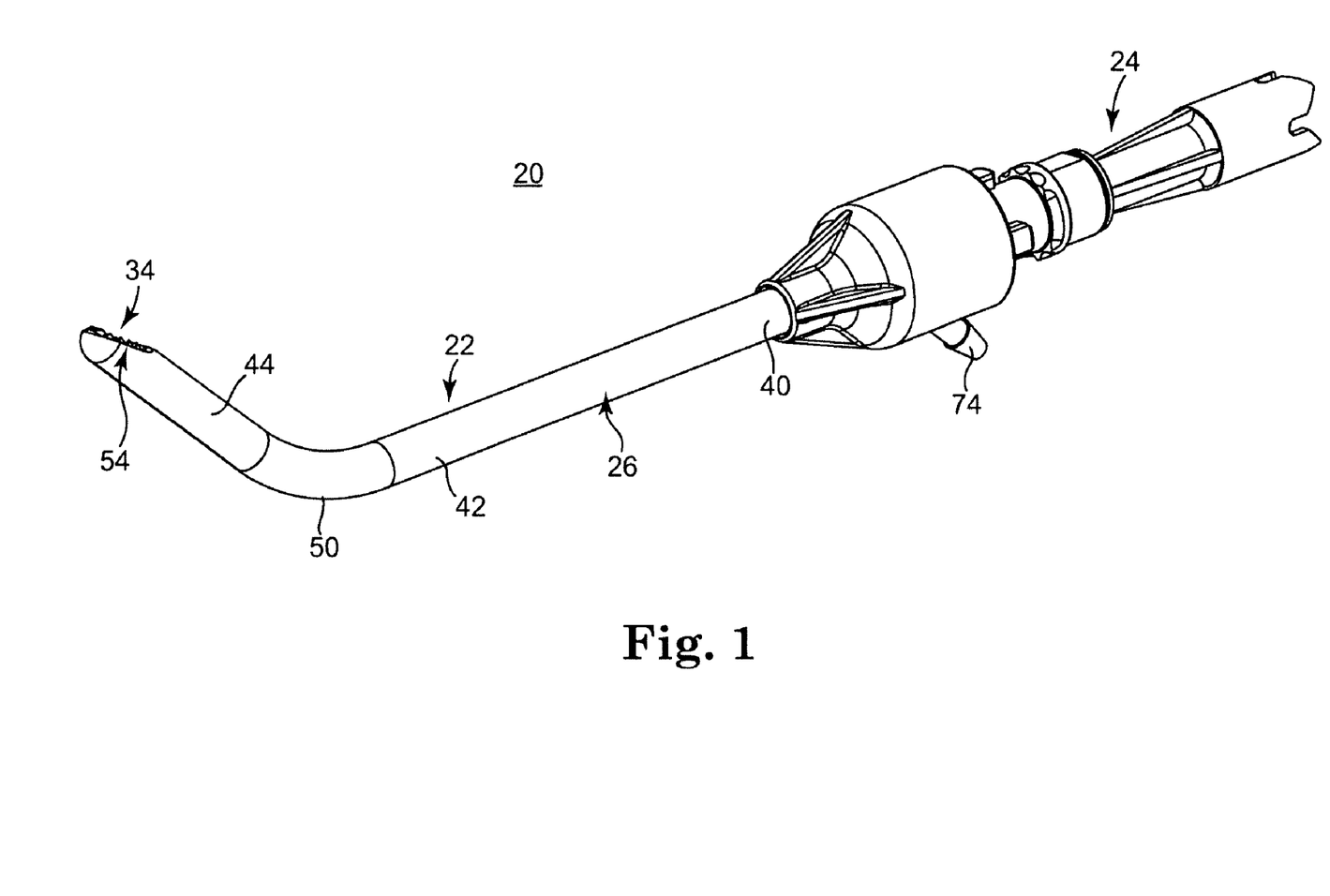
FIG. 1 is a perspective view of an intervertebral disc material shaving instrument in accordance with aspects of the present invention.
Figure 2:
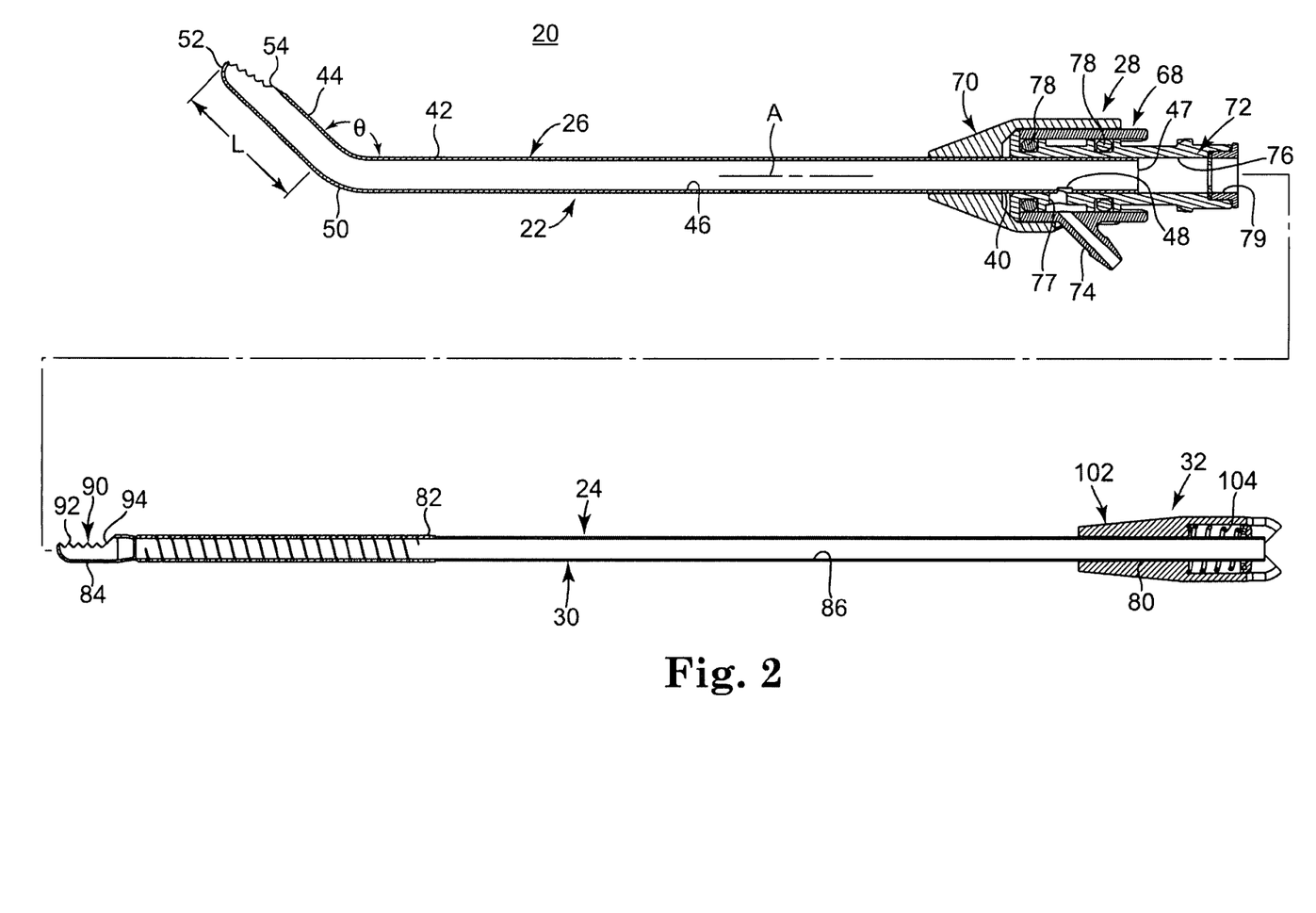
FIG. 2 is a cross-sectional, partial exploded view of the instrument of FIG. 1.

One embodiment of an intervertebral disc shaving instrument 20 in accordance with the principles of the present invention is shown in FIGS. 1 and 2. The instrument 20 includes an outer tubular assembly 22 and an inner tubular assembly 24. The outer tubular assembly 22 includes an outer tubular member 26 and a first hub assembly 28. Similarly, the inner tubular assembly 24 includes an inner tubular member 30 (best seen in FIG. 2) and a second hub assembly 32. Details on the various components are provided below. In general terms, however, the inner tubular member 30 is coaxially disposed within the outer tubular member 26, with the tubular members 26, 30 combining to define a bodily material shaving head 34 (FIG. 1). During use, the instrument 20 is coupled to a powered handpiece (not shown) that rotates the second hub assembly 32, and thus the inner tubular member 30, relative to the outer tubular member 26 in an oscillating fashion, to effectuate shearing of intervertebral disc material (not shown) at the shaving head 34.

The outer tubular member 26 is an elongated body defining a proximal segment 40, an intermediate segment 42, and a distal segment 44. Further, the outer tubular member 26 defines a central passage 46 (FIG. 2) extending from the distal segment 44 to the proximal segment 40.

With specific reference to FIG. 2, the proximal segment 40 is adapted for connection to the first hub assembly 28, and defines a longitudinal axis A. For example, the proximal segment 40 forms a proximal open end 47 and a radial aperture 48 both of which are open to the central passage 46. As described below, the open end 47 facilitates placement of the inner tubular member 30 within the central passage 46, whereas the aperture 48 establishes fluid connection between the central passage 46 and a corresponding component of the first hub assembly 28. Alternatively, the proximal segment 40 can assume a variety of other forms.

The intermediate segment 42 extends from the proximal segment 40 to the distal segment 44 and forms a bend 50. In one embodiment, the distal segment 44 is linear in longitudinal extension. Thus, due to the bend 50, the distal segment 44 extends at or forms a bend angle Θ relative to the longitudinal axis A of the proximal segment 40. The bend angle Θ is selected to facilitate desired positioning of the distal segment 44 (and thus of the tissue shaving head 34) within an intervertebral disc space (not shown) using an expected surgical approach to the disc space as described below. With this in mind, the bend angle Θ is in the range of 0-90°. For example, it has surprisingly been found that for posterior disc approach applications, the bend angle Θ is preferably in the range of 20-45°, more preferably 45°. It has further been surprisingly found that for lateral disc approach procedures, the bend angle Θ is preferably in the range of 0-12.5°, more preferably 12.5°. Notably, however, principles of the present invention are not limited to a particular value or range for the bend angle Θ. Along these same lines, two or more bends can be provided along a length of the outer tubular member 26 (e.g., along one, two, or all of the segments 40-44). Further, the bend 50 can be formed at a longitudinal position varying from that shown in FIGS. 1 and 2 (e.g., along the proximal segment 40). Preferably, however, a length L of the distal segment 44 (i.e., linear distance from a distal termination point of the bend 50 to a distal-most end 52 of the distal segment 44) is in the range of 1.5-3.5 cm, more preferably 2.5 cm. It has surprisingly been found that by forming a "working end" of the instrument 20 to have a length of 2.5 cm is highly conducive to cutting operation within an intervertebral disc via a posterior lumbar approach (e.g., as part of a posterior lumbar intervertebral fusion operation). Notably, the length L can vary in other embodiments.

As mentioned above, the distal segment 44 terminates at the distal end 52 that is preferably closed to the central passage 46. Further, the distal segment 44 forms a cutting window 54 proximal the closed distal end 52. As described in greater detail below, the closed distal end 52 serves to distally shield a cutting surface of the inner tubular member 30, whereas the cutting window 54 exposes the surface. Thus, in one embodiment, an exterior surface of the closed distal end 52 is curved.

Figure 3A:
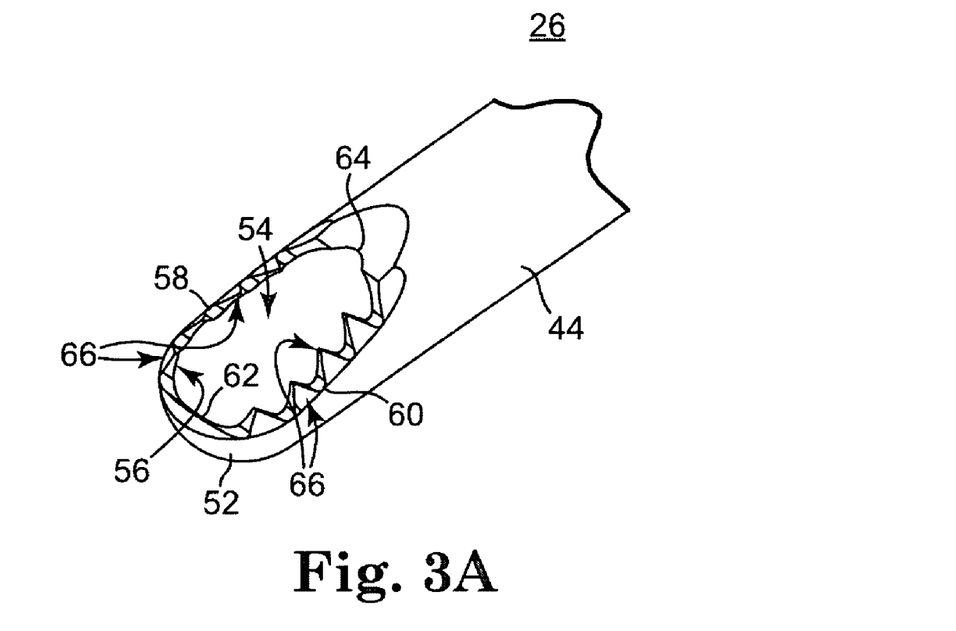
FIG. 3A is an enlarged top plan view of a distal segment of an outer tubular member portion of the instrument of FIG. 1.
Figure 3B:
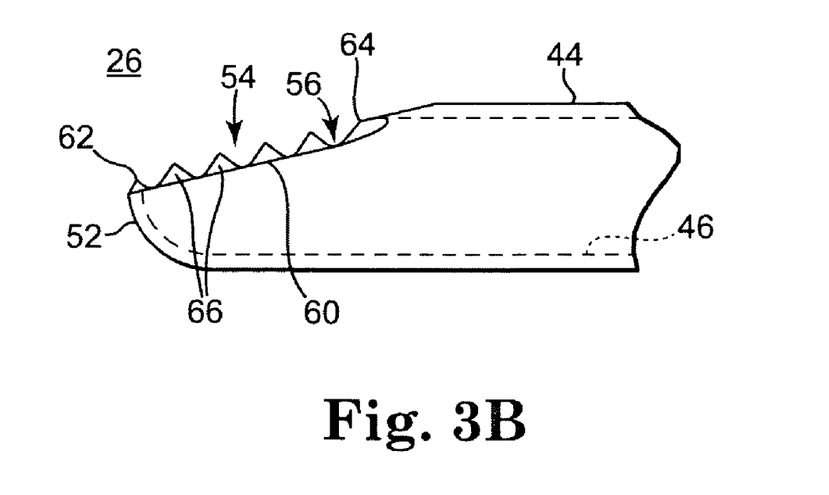
FIG. 3B is a side view of the segment of FIG. 3A.

With reference to FIGS. 3A and 3B, the cutting window 54 is open or fluidly connected to the central passage 46, and is defined by a perimeter edge 56. Relative to a longitudinal extension of the outer tubular member 26, the perimeter edge 56 generally defines opposing first and second longitudinal sides 58, 60, and opposing lateral ends 62, 64. With these spatial designations in mind, in one embodiment, the perimeter edge 56 forms a plurality of teeth 66 along each of the longitudinal sides 58, 60. The teeth 66 can assume a variety of forms, but in one embodiment are symmetrically arranged relative to the side 58, 60. In one embodiment, each of the sides 58, 60 includes or forms at least four teeth 66 to promote aggressive removal of intervertebral disc material. The teeth 66 are formed to be highly sharpened (e.g., tip width or thickness on the order of approximately 0.005 inch), and wrap or curve in conformance with a curvature of the remainder of the outer tubular member 26. In one embodiment, a tip-to-tip spacing between adjacent ones of the teeth 66 (along a corresponding side 58 or 60) is in the range of 0.04-0.06 inch, more preferably approximately 0.05 inch (±0.002 inch). Further, in one embodiment, the lateral ends 62, 64 are similarly sharp. While other dimensions and/or configurations can be employed, it has surprisingly been found that the above-described preferences are highly conducive to cutting the disparate material structures associated with an intervertebral disc.

Returning to FIG. 2, the outer tubular member 26 is preferably formed of a hardened, surgically safe material, capable of supporting the inner tubular member 30 at high rotational/ oscillation speeds (e.g., oscillation speed of 5,000 RPM), while maintaining the bent shape illustrated. Thus, for example, the outer tubular member 26 is formed of 304 stainless steel; although a multitude of other materials are equally acceptable. Regardless, the central passage 46 is sized to coaxially receive the inner tubular member 30 in a manner allowing the inner tubular member 30 to rotate within the passage 46. In one embodiment, and as described below, a diameter of the central passage 46 is slightly greater than an outer diameter of the inner tubular member 30 to establish an irrigation pathway.

The first hub assembly 28 is adapted to receive and retain the proximal segment 40 of the outer tubular member 26, and in one embodiment includes an irrigation collar 68, an outer hub 70, and an inner hub 72. The irrigation collar 68 forms an irrigation port 74, and is configured to establish an irrigation fluid flow path to and from the central passage 46 of the outer tubular member 26 upon final assembly, as described below. The outer hub 70 and the inner hub 72 are adopted to secure the irrigation collar 68 to the outer tubular member 26, and thus can assume a variety of forms. In one embodiment, however, the outer hub 70 is sized for securement over the irrigation collar 68 as well as to the outer tubular member 26. Conversely, the inner hub 72 is sized for securement between the irrigation collar 68 and the outer tubular member 26, and in one embodiment forms a longitudinal passageway 76 and a radial opening 77. The longitudinal passageway 76 extends through an entirety of the inner hub 72, whereas the radial opening 77 is sized and positioned for fluid connection to the port 74 (and the radial aperture 48 of the outer tubular member 26) upon final assembly. To further promote a complete, sealed final relationship, the first hub assembly 28 further includes seals (e.g., O-rings) 78 and a seal hub 79 in one embodiment. Regardless, the first hub assembly 28 establishes a mechanism for delivering irrigation liquid from an irrigation source (not shown) to the shaving head 34 via the irrigation port 74 and the passage 46. The irrigation fluid serves to "clean" the surgical site, augment lubrication between the inner and outer tubular members 30, 26, and facilitate evacuation/aspiration of material from the surgical site (described below) by clearing "clogs" at the shaving head 34. Alternatively, the first hub assembly 28 can assume a variety of other forms.

The inner tubular member 30 is, similar to the outer tubular member 26, an elongated tube defining a proximal region 80, an intermediate region 82, and a distal region 84. Further, the inner tubular member 30 defines a central lumen 86 extending from the proximal region 80 to the distal region 84. Once again, the inner tubular member 30 is sized to be coaxially received within the outer tubular member 26, with the proximal region 80 adapted for mounting to the second hub 32. In one embodiment, at least the intermediate region 82 has a flexible construction such that the inner tubular member 30 will assume the shape of the outer tubular member 26 (and in particular the bend 50) upon insertion of the inner tubular member 30 within the outer tubular member 26. For example, the intermediate region 82 can be or includes a wound coil(s) or reinforced tube(s) (e.g., inner and outer spiral wraps assembled over a spiral cut formed in the outer tubular member 30), series of laser cut dovetail sections, etc. (it being understood that the intermediate region 82 is illustrated generally in FIG. 2). Regardless, while the regions 80-84 may have differing constructions (e.g., the proximal and distal regions 80, 84 are metal tubes, whereas the intermediate region 82 is a wound coil), the inner tubular member 30 has an overall construction capable of maintaining structural integrity when rotated at high speeds (e.g., oscillation speeds on the order of 5,000 RPM).

The distal region 84 forms a cutting tip 90. With additional reference to FIG. 3C, the cutting tip 90 includes a plurality of teeth 92 formed in a circumferentially-extending manner about a mouth 94. The teeth 92 are highly similar to the teeth 66 (FIGS. 3A and 3B) previously described, symmetrically arranged along opposite sides of the mouth 94 (it being understood that only one set of the teeth 92 are visible in FIG. 3C). Thus, in one embodiment, at least four of the teeth 92 are formed along each side of the mouth 94, and are highly sharpened. Further, in one embodiment, the teeth 92 are sized and positioned to be spatially aligned with the teeth 66 upon final assembly. Thus, in one embodiment, adjacent ones of the teeth 92 have a tip-to-tip spacing on the order of 0.04-0.06 inch, more preferably approximately 0.05 inch (±0.002 inch).

The mouth 94 is open to, and thus fluidly connected with, the lumen 86. As described in greater detail below, this configuration establishes an aspiration pathway from the mouth 94 and through the lumen 86. In this regard, material aspirated via the lumen 86/mouth 94 can be removed via an appropriate port associated with the second assembly hub 32. In one embodiment, the distal region 84 has a relatively large outer diameter, on the order of 3-8 mm, more preferably 4.5 mm, to reduce clogging of the lumen 86 during use. Alternatively, other dimensions can be employed.

Figure 3C:
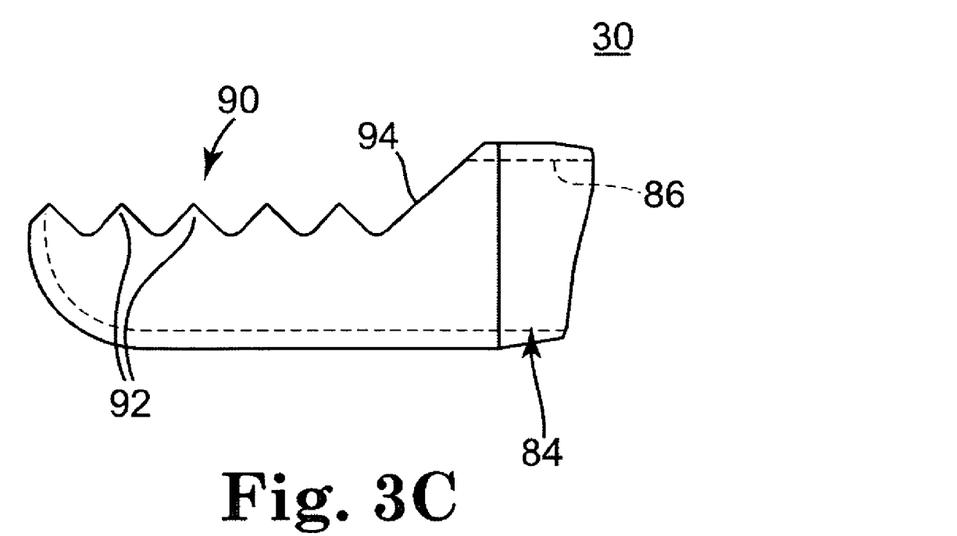
FIG. 3C is an enlarged, top plan view of a distal segment of an inner tubular member portion of the instrument of FIG. 1.
Figure 3D:
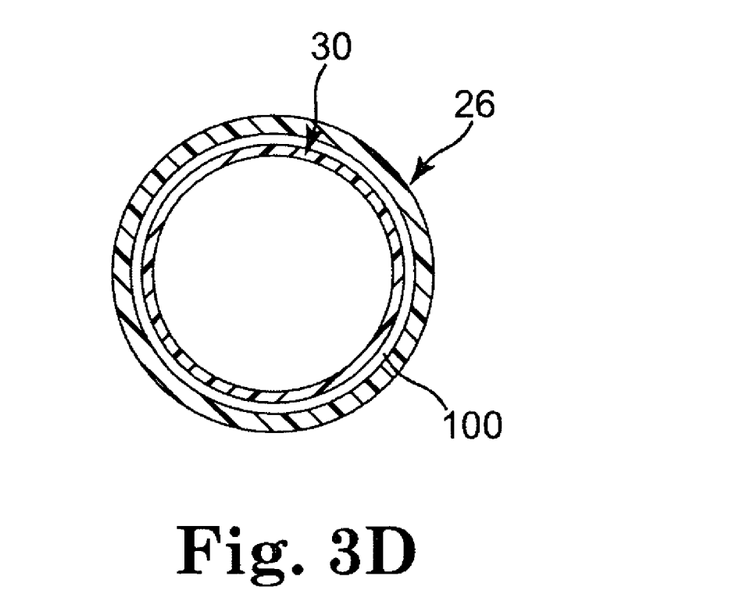
FIG. 3D is a cross-sectional view of the assembled instrument of FIG. 1.

Regardless of the exact configuration, at least as a majority of an inner diameter of the outer tubular member 26 is, in one embodiment, slightly larger than an outer diameter of the inner tubular member 30 so as to establish an annular gap 100 between the two components 26, 30 upon final assembly as shown in FIG. 3D. It will be understood that while FIG. 3D illustrates the inner tubular member 30 as being approximately centered relative to the outer tubular member 26, in actual practice, the inner tubular member 30 may contact the outer tubular member 26 at various radial locations. Along these lines, in one embodiment, the cutting tip 90 (FIG. 3C) of the inner tubular member 30 may have a diameter larger than a remainder thereof (such as by separately forming the cutting tip 90 and assembling to a remainder of the inner tubular member 30) that more closely matches an inner diameter of the outer tubular member 26. Regardless, a size of the gap 100 is exaggerated in the view of FIG. 3D for purposes of explanation. With additional reference to FIGS. 1 and 2, the annular gap 100 extends from the irrigation port 74 to the cutting window 54 to establish an interior irrigation pathway or mechanism by which an irrigation fluid can be delivered from the irrigation port 74 to the cutting window 54 (and thus the shaving head 34) via the annular gap 100. Alternatively, a separate irrigation tube (not shown) can be provided along (or formed with) an exterior of the outer tubular member 26.

With specific reference to FIG. 2, the second hub assembly 32 is sized for mounting to the inner tubular member 30 and includes, in one embodiment, a rotating hub 102 and a spring 104. The rotating hub 102 is adapted for coupling to a powered handpiece (not shown) as known in the art. The spring 104 facilitates releasable engagement with the powered handpiece, and in alternative embodiments, can be eliminated. To this end, the powered handpiece can assume a variety of forms, and can be electrically, or battery, or pneumatically powered.

Assembly of the instrument 20 includes securing the first hub assembly 28 to the outer tubular member 26. In one embodiment, the inner hub 72 is mounted over the proximal segment 40 such that the radial opening 77 is aligned, or otherwise fluidly connected to, the radial aperture 48. To ensure affixment of the inner hub 72 to the outer tubular member 26, an adhesive (e.g., Loctite adhesive) can be employed. The irrigation collar 68 is mounted over the inner hub 72 such that the port 74 is aligned with, or otherwise fluidly connected to, the radial opening 77 (and thus the radial aperture 48). The seals 78 are included at opposite sides of the port 74/radial opening 77 interface to provide a fluid-sealed relationship. The outer hub 70 is assembled or formed over the outer tubular member 26 and the irrigation collar 68. Where desired, an adhesive (e.g., Loctite adhesive) can be employed to bond the outer hub 70 to the irrigation collar 68.

The second hub assembly 32 is mounted to the proximal region 80 of the inner tubular member 30. An adhesive can be employed to bond the rotating hub 102 to the inner tubular member 30. The inner tubular member 30 is distally slid or inserted into and through the inner hub 72 and the outer tubular member 26 such that the cutting tip 90 is at or within the cutting window 54. To this end, the seal hub 79 sealingly engages an exterior of the inner tubular member 30 such that irrigation fluid within the outer tubular member 26 (e.g., within the gap 100 (FIG. 3D)) will not flow or leak proximal the seal hub 79.

Figure 4:
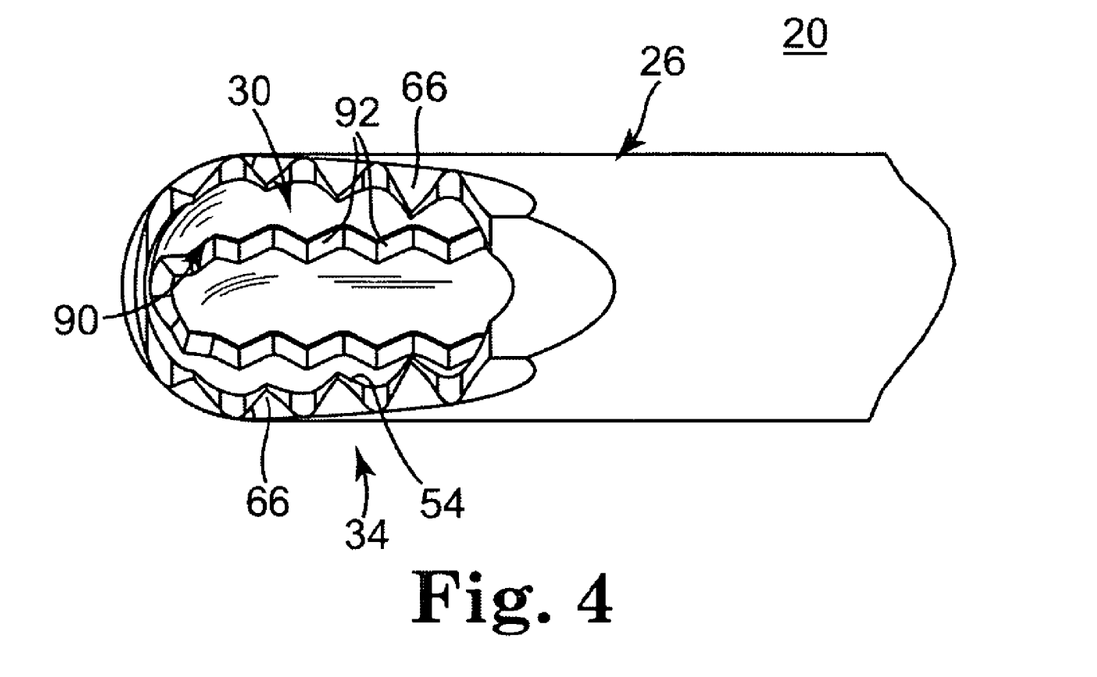
FIG. 4 is an enlarged, top plan view of the material shaving head formed by the instrument of FIG. 1

The shaving head 34 upon final assembly is shown in greater detail in FIG. 4. In particular, the cutting tip 90 is exposed at the cutting window 54. During use, as the inner tubular member 30 is rotatably oscillated relative to the outer tubular member 26, a shearing action is created between the teeth 92 of the cutting tip 90 and the teeth 66 of the cutting window 54. By providing a large number of sharp teeth, this shearing motion is able to aggressively remove material, yet provides a user with the ability to perform a controlled shaving or shearing operation, thus ensuring that only desired bodily material is contacted and cut. To this end, the closed distal end 52 of the outer tubular member 26 provides a blunt surface for non-traumatically contacting anatomical structures, thus providing instrument safety during "blind" cutting procedures.

Figure 5:
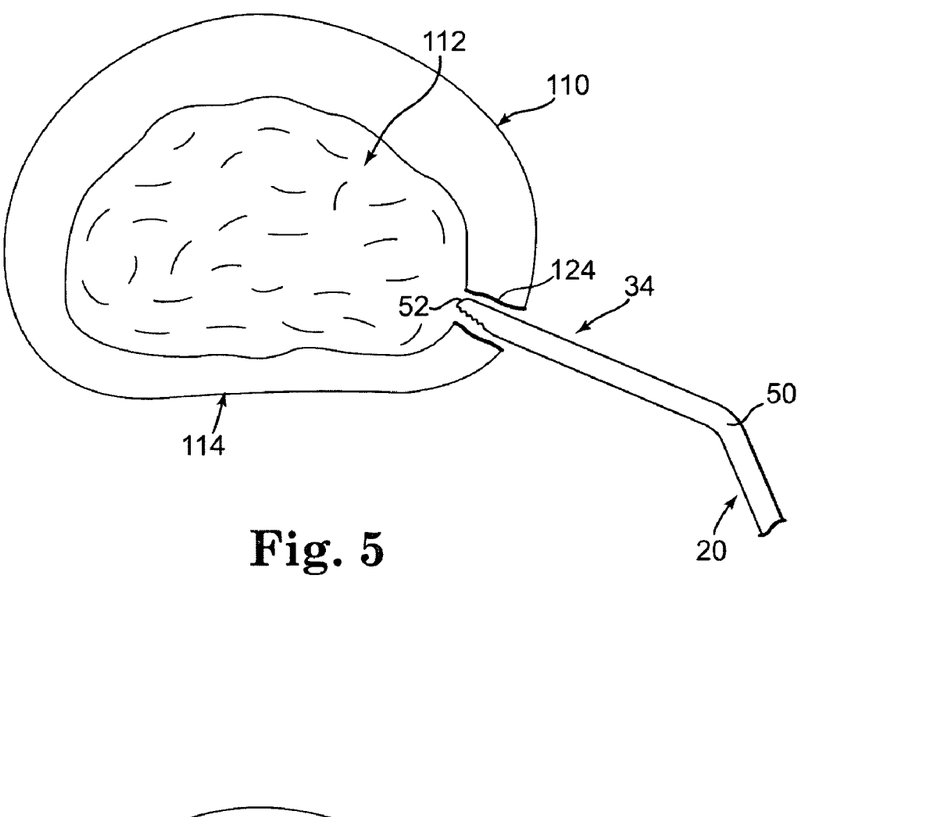
FIG. 5 is a simplified, top plan view of an intervertebral disc in combination with the instrument of FIG. 1 upon initial approach.
Figure 6:
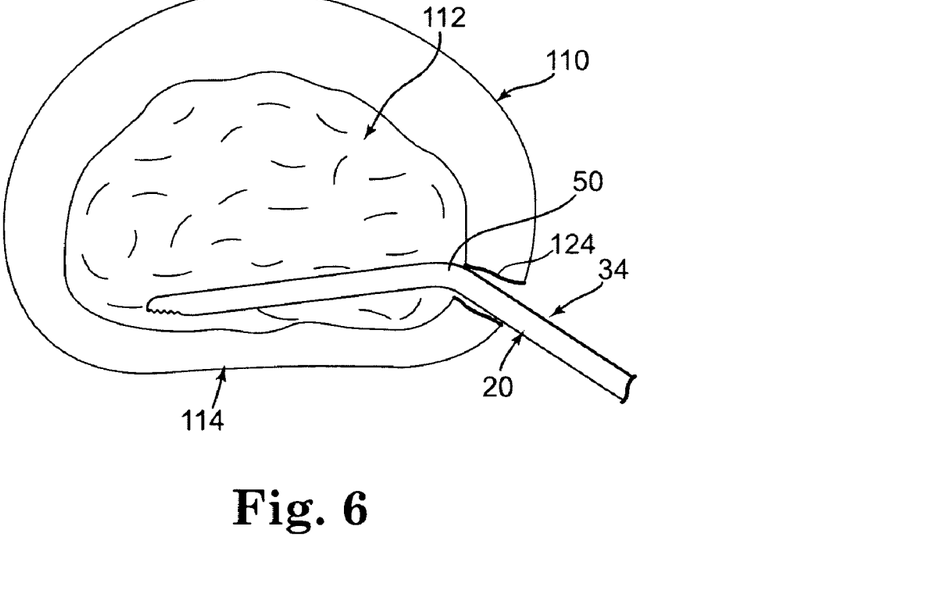
FIG. 6 is the view of FIG. 5 with the instrument fully inserted.
Figure 7:
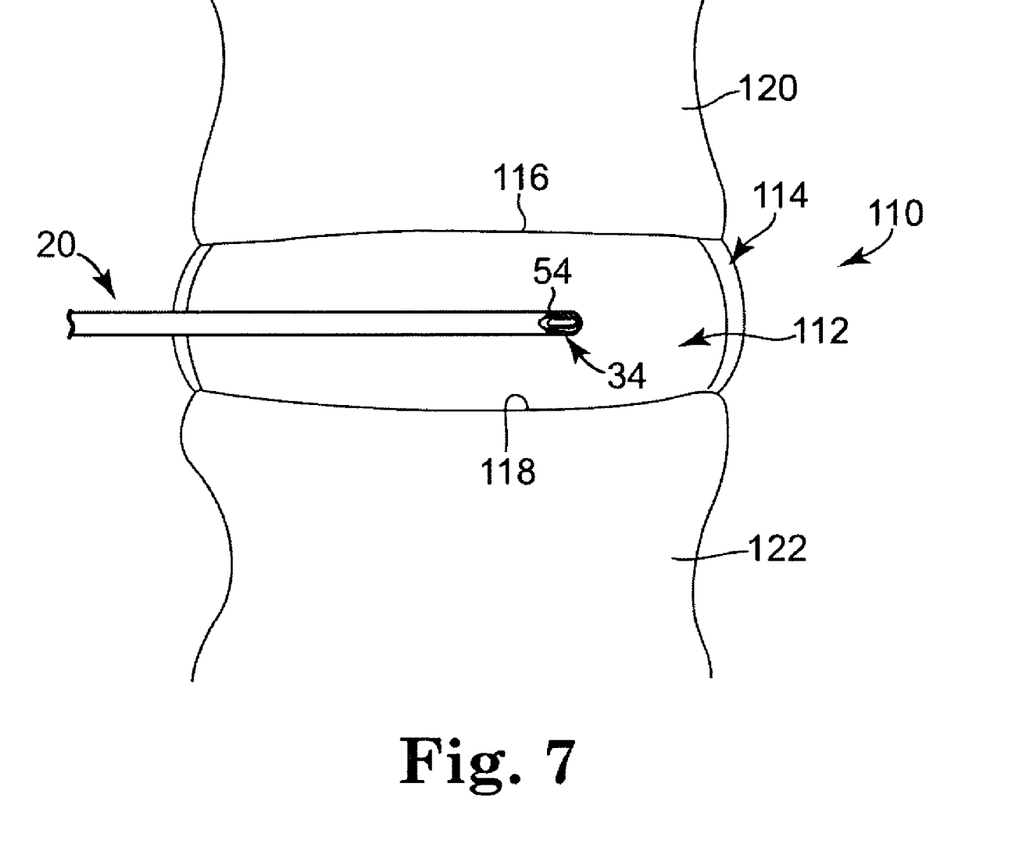
FIG. 7 is a simplified, side cross-sectional view of FIG. 6.

One method of removing material from an intervertebral disc 110 using the intervertebral disc material shaving instrument 20 in accordance with principles of the present invention is illustrated in FIGS. 5-7. By way of reference, the intervertebral disc 110 generally includes a nucleus 112 surrounded by an annulus 114 and opposing ends plates 116, 118 (FIG. 7). The end plates 116, 118 in turn, are formed as part of adjacent vertebrae 120, 122 (FIG. 7), respectively, and thus are akin to cartilaginous bone. With these general definitions in mind, the instrument 20 is employed to surgically remove or shave some or all of the material (e.g., tissue, cartilaginous bone, etc.) associated with the intervertebral disc 110. For example, one common procedure associated with treatment of a diseased intervertebral disc 110 is a nucleotomy in which a portion, or all, of the nucleus 112 is removed. With this in mind, the instrument 20 is deployed to the disc 110, for example via an posterior-lateral approach. Alternative approaches to the disc 110 are also acceptable and within the principles of the present invention, such as posterior approach, transforaminal approach, anterior approach, left or right lateral approach, etc. Regardless, as shown in FIG. 5, the shaving head 34 is positioned at an exterior of the annulus 114, aligned with an opening 124 formed therein. The opening 124 can be a naturally-occurring tear or similar passage; alternatively, the opening 124 can be surgically cut or otherwise created in the annulus 114. The closed distal end 52 contacts the annulus 114 in a non-traumatic manner, and protects the annulus 114 from potentially damaging, undesired contact with the teeth 66 (FIG. 3A) and 92 (FIG. 3C).

The shaving head 34 is then distally advanced within the annulus 114, with the bend 50 facilitating desired extension of the shaving head 34 "across" the nucleus 112 region as shown in FIG. 6. That is to say, the bend 50 is configured to anatomically "match" the expected insertion site of the tissue shaving head 34 relative to the opening 124 in the annulus 114 (that is otherwise offset from a "center" of the disc 110 so as to avoid contact with other bodily structures such as nerves). Thus, the bend angle Θ (FIG. 2) is a function of the expected disc 110 approach location. With the shaving head 34 properly positioned, the bend 50 generally resides at the annulus 114.

Regardless of the exact positioning, the instrument 20 is powered to effectuate removal of contacted material. More particularly, and with additional reference to FIG. 7, the powered handpiece (not shown) is activated, causing the cutting tip 90 (FIG. 3C) to rotationally oscillate relative to the cutting window 54. For example, the cutting tip 90 can be rotationally oscillated at speeds at or in excess of 5,000 RPM. In one embodiment, the powered handpiece is operated to rotate the inner tubular member 26 (FIG. 2) two revolutions in one direction, followed by two revolutions in the opposite direction, etc., although other operational formats are also acceptable. Nucleus tissue 112, otherwise in contact with the cutting tip 90/cutting window 54, is sheared between the two components, and aspirated from the surgical site via the mouth 94/lumen 86 (FIG. 2). Further, irrigation fluid is directly applied to the surgical site via the irrigation mechanism previously described so as to minimize clogging of the tissue shaving head 34, and in particular the mouth 94/lumen 86. The irrigation fluid can also serve to lubricate the surgical site as well as the inner tubular member 30/outer tubular member 26 interface.

While the instrument 20 has been described in connection with performing a nucleotomy, other material of the intervertebral disc 110 can also be aggressively shaved or sheared with the instrument 20. For example, the annulus 114 tissue and/or end plate 116, 118 cartilaginous bone can also be shaved/sheared as desired.

Although the present invention has been described with reference to preferred embodiments, workers skilled in the art will recognize that changes can be made in form and detail without departing from the spirit and scope of the present invention.

What is claimed is:

1. A method for removing material of an intervertebral disc defined by a nucleus surrounded by an annulus and opposing end plates, the method comprising:
   obtaining a surgical shaving instrument including:
      an elongated outer tubular member defining a closed distal end, a central passage and a cutting window at a distal segment thereof, the cutting window having a perimeter edge and being fluidly connected to the central passage;
      an inner tubular member coaxially disposed within the central passage, the inner tubular member defining a central lumen and a cutting tip at a distal region thereof, the cutting tip including a plurality of teeth formed about a mouth otherwise fluidly connected to the lumen,
      wherein upon final assembly, the cutting tip is exposed within the cutting window, and the cutting tip and cutting window combine to define a shaving head;
   coupling the inner tubular member to a powered handpiece, wherein the powered handpiece is adapted to cause the inner tubular member to rotate relative to the outer tubular member;

inserting the shaving head through the annulus and into the intervertebral disc, including the closed distal end directly contacting and passing through the annulus while the cutting tip is not activated;
positioning the shaving head such that the cutting tip contacts targeted material of the intervertebral disc;
activating the powered handpiece to rotate the cutting tip relative to the cutting window;
shearing the contacted intervertebral disc material between the perimeter edge of the cutting window and the teeth of the cutting tip; and
aspirating the sheared intervertebral disc material through the lumen via the mouth.

2. The method of claim 1, wherein shearing the contacted intervertebral disc material includes rotatably oscillating the inner tubular member relative to the outer tubular member about a central axis of the inner tubular member.

3. The method of claim 2, wherein the perimeter edge of the cutting window define first and second opposing longitudinal sides, and further wherein shearing the contacted intervertebral disc material includes alternately shearing tissue against the first side and the second side.

4. The method of claim 1, wherein the surgical instrument further includes an irrigation mechanism fluidly connecting an irrigation source to the shaving head, the method further comprising:
irrigating the shaving head following insertion within the intervertebral disc via the irrigation mechanism.

5. The method of claim 4, wherein the method is characterized by simultaneously irrigating the shaving head and aspirating sheared material.

6. The method of claim 4, wherein the irrigation mechanism includes an irrigation port provided at a proximal segment of the outer tubular member and fluidly connected to an annular gap defined between the inner tubular member and the outer tubular member, the annular gap fluidly connected to the cutting window to complete an interior fluid path from the irrigation port to the cutting window.

7. The method of claim 1, wherein the outer tubular member defines a bend point along the longitudinal length thereof, and further wherein inserting the shaving head includes:
directing the shaving head distally through an opening in the annulus; and
positioning the bend at the annulus.

8. The method of claim 1, wherein the cutting tip has a diameter in the range of 3-8 MM.

9. The method of claim 8, wherein the cutting tip has a diameter of 4.5 mm.

10. The method of claim 1, wherein the perimeter edge of the cutting window defines at least eight teeth.

11. The method of claim 1, wherein the sheared material is nucleus tissue.

12. The method of claim 1, wherein the sheared material is annulus tissue.

13. The method of claim 1, wherein the sheared material is cartilaginous end plate bone.

14. The method of claim 1, wherein the outer tubular member defines a bend point along a longitudinal length thereof and having a bend angle of 45°, and further wherein inserting the shaving head includes:
posteriorly approaching the intervertebral disc with the shaving head; and
positioning the bend point at the annulus.

15. The method of claim 1, wherein the outer tubular member defines a bend point along a longitudinal length thereof and having a bend angle of 12.5°, and further wherein inserting the shaving head includes:
laterally approaching the intervertebral disc with the shaving head; and
positioning the bend point at the annulus.

16. The method of claim 1, wherein a perimeter of the mouth of the inner tubular member forms at least eight spaced apart teeth between proximal and distal ends thereof, and further wherein the perimeter edge of the outer tubular member fauns at least eight spaced apart teeth between proximal and distal ends thereof, the teeth configured to cut disparate material structures of the intervertebral disc.

17. The method of claim 1, wherein the step of inserting the shaving head through the annulus and into the intervertebral disc is performed in the absence of an outer cannula and wherein the cutting tip remains fixed relative to the cutting window in a longitudinal direction of the outer tubular member.

* * * * *

UNITED STATES PATENT AND TRADEMARK OFFICE
CERTIFICATE OF CORRECTION

PATENT NO.        : 7,927,361 B2                                Page 1 of 1
APPLICATION NO.   : 11/289266
DATED             : April 19, 2011
INVENTOR(S)       : Dana A. Oliver et al.

It is certified that error appears in the above-identified patent and that said Letters Patent is hereby corrected as shown below:

Column 10, line 5, delete "3-8MM" and insert in place thereof --3-8mm--.

Column 10, line 33, delete "member fauns" and insert in place thereof --member forms--.

Signed and Sealed this
Tenth Day of January, 2012

David J. Kappos
*Director of the United States Patent and Trademark Office*